(12) United States Patent
Strukelj

(10) Patent No.: US 6,605,688 B2
(45) Date of Patent: *Aug. 12, 2003

(54) LOW VISCOSITY IMINE REACTIVE DILUENTS AND COATING COMPOSITIONS MADE THEREFROM

(75) Inventor: Marko Strukelj, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/007,354

(22) Filed: Nov. 9, 2001

(65) Prior Publication Data

US 2002/0123607 A1 Sep. 5, 2002

Related U.S. Application Data

(63) Continuation-in-part of application No. 09/335,542, filed on Jun. 18, 1999, now Pat. No. 6,399,742.
(60) Provisional application No. 60/090,194, filed on Jun. 22, 1998.

(51) Int. Cl.$^7$ .......................... C08G 18/00; C08K 5/00; C08L 75/00; C09D 133/04
(52) U.S. Cl. .......................... 528/332; 528/82; 528/113; 528/114; 528/118; 528/121; 528/229; 528/288; 528/363; 528/59; 525/113; 525/127; 525/176; 525/330.5; 525/440; 525/438; 525/445; 525/449; 525/437; 525/454; 525/533; 525/524; 525/528; 560/168; 427/384; 427/385.5; 427/386

(58) Field of Search .......................... 525/437, 330.5, 525/438, 440, 445, 449, 127, 113, 176, 454, 533, 524, 528; 528/59, 82, 113, 114, 288, 363, 118, 229, 121; 560/168; 427/384, 385.5, 386

(56) References Cited

U.S. PATENT DOCUMENTS

| | | | |
|---|---|---|---|
| 3,668,183 A | 6/1972 | Hoy et al. | |
| 4,772,680 A | 9/1988 | Noomen et al. | |
| 5,011,994 A | 4/1991 | Bartels et al. | |
| 5,198,524 A | 3/1993 | Bush et al. | |
| 5,288,802 A | 2/1994 | Walters et al. | |
| 6,365,673 B1 * | 4/2002 | Corcoran et al. | 525/113 |
| 6,399,742 B1 * | 6/2002 | Strukelj | 528/332 |

FOREIGN PATENT DOCUMENTS

| | | |
|---|---|---|
| EP | 967198 A1 | 12/1999 |
| WO | WO 94/27746 | 12/1994 |
| WO | WO 97/39063 | 10/1997 |

* cited by examiner

*Primary Examiner*—P. Hampton-Hightower
(74) *Attorney, Agent, or Firm*—Sudhir G. Deshmukh

(57) ABSTRACT

This invention concerns low viscosity aldimine and ketimine reactive diluents having multi-imine functionality, which are useful in automotive refinish coating compositions, including a process for making them and the coatings that contain them.

8 Claims, No Drawings

LOW VISCOSITY IMINE REACTIVE DILUENTS AND COATING COMPOSITIONS MADE THEREFROM

BACKGROUND OF THE INVENTION

The present invention relates to curable compositions and more particularly to low VOC (volatile organic component) ambient temperature curable coating compositions containing low viscosity imine reactive diluents, which are especially suited for use in automotive refinish applications.

Due to increasingly stringent environmental regulations and the demand for better performance, reactive diluents/oligomers are becoming crucial components in a variety of automotive coating formulations. This is especially true for high solids coatings. Such products are typically enamels because low molecular weight building blocks can be used to form cross-linked networks that provide robust films. The rate of cure is therefore important since the rate of film formation determines autobody shop throughput and profitability. Certain imines and imine-containing coating compositions are known. Representative disclosures can be found in U.S. Pat. Nos. 5,198,524, 3,668,183, 4,772,680 and 5,288,802. None of these publications discloses the imines of this invention nor coatings that contain them characterized by low volatile organic content (VOC), good sprayability, quick cure and hard, solvent-resistant films formed therefrom.

SUMMARY OF THE INVENTION

The present invention is directed to an imine reactive diluent of Formula I:

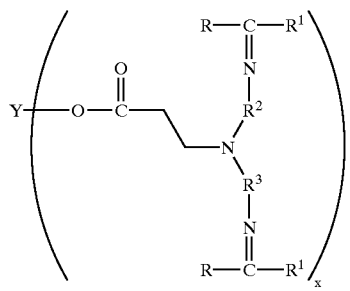

I wherein

R and $R^1$ are the same or different, and are independently selected from the group consisting of hydrogen, a $C_6$ to $C_{50}$, preferably $C_6$ to $C_{14}$, more preferably $C_6$ to $C_8$ aromatic structure, $C_1$ to $C_{50}$ alkyl moiety having a linear aliphatic, branched aliphatic, or cycloaliphatic structure. When the alkyl moiety has the cycloaliphatic structure it preferably includes 6 to 14 carbon atoms, when it has the linear or branched structure it preferably includes 1 to 10 carbon atoms.

$R^2$ and $R^3$ are the same or different, and are selected from the group consisting of a $C_1$ to $C_{50}$, preferably $C_1$ to $C_{10}$, more preferably $C_1$ to $C_5$ linear aliphatic, branched aliphatic, and cycloaliphatic structure. When $R^2$ and $R^3$ have the cycloaliphatic structure they preferably include 6 to 14 carbon atoms, when they have the linear structure they preferably include 2 to 10 carbon atoms and when they have the branched structure they preferably include 3 to 10 carbon atoms.

Y is a residue with a weight average molecular weight up to about 100,000, preferably 14 to 100,000, more preferably 14 to 50,000, most preferably 28 to 20,000 and having said linear aliphatic, branched aliphatic, cycloaliphatic, aromatic structure, or a combination thereof;

wherein R, $R^1$, $R^2$, $R^3$ and Y are free from a hydrogen bonding group; and x is an integer of at least 2, preferably 2 to 50, more preferably 2 to 10 and most preferably 2 to 4. Preferred imine reactive diluents of Formula I are those in which R and $R^1$ are not both isopropyl.

$R^2$, $R^3$ or Y of the imine reactive diluent of Formula I may include one or more heteroatoms, preferably 1 to 3 heteroatoms in $R^2$ and $R^3$, and preferably 1 to 30 in Y. Preferred heteroatoms include O, S, Si and P but not N. To achieve good coating solution viscosity, there will be no hydrogen atoms on any of the heteroatoms.

The imine reactive diluent 1 is a ketimine when R and $R^1$ are not hydrogen and an aldimine when $R^1$ is not hydrogen.

Some of the preferred imine reactive diluent of Formula I include the following:

(a) Y is —$(CH_2)_6$— and x=2;

(b) Y is:

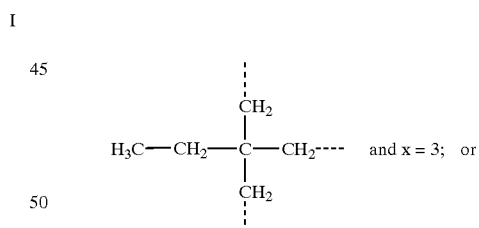 and x = 3; or (c) Y is:

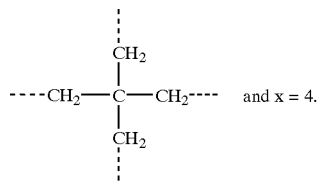 and x = 4.

Even more preferred imine reactive diluents of Formula I is:
I. A tetraketimine having the formula:
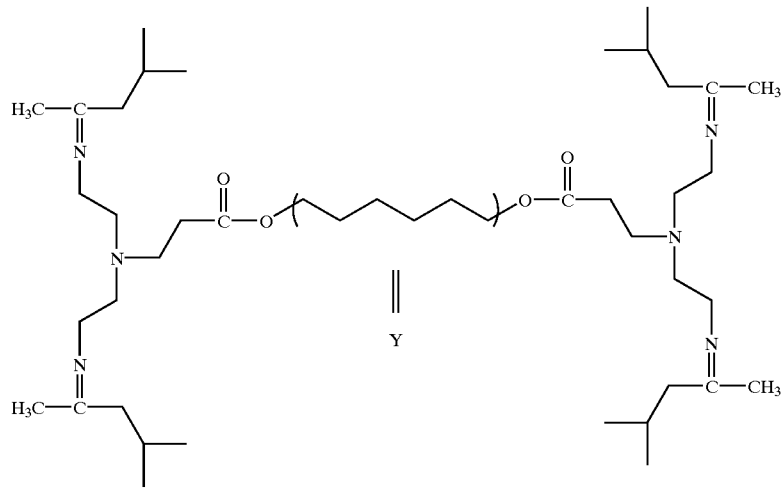
when Y is (a).
II. A hexaketimine having the formula:
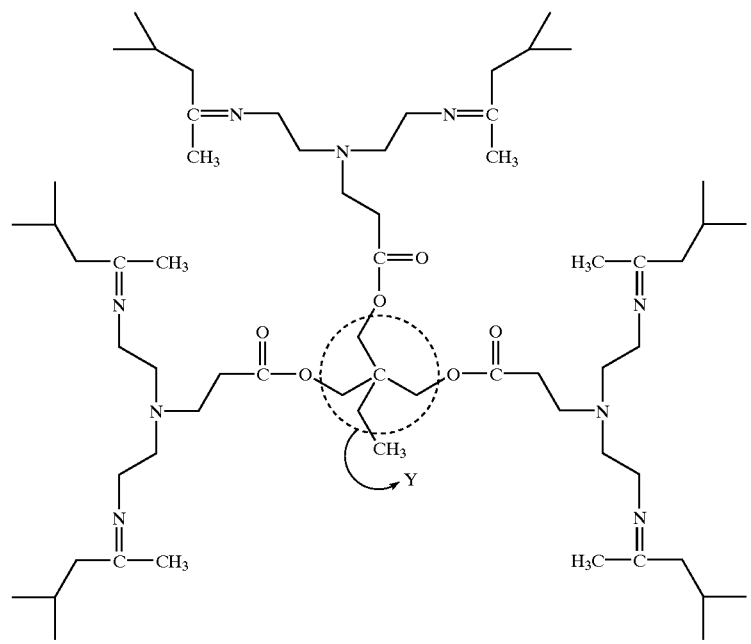
when Y is (b).

III. An octaketimine having the formula:

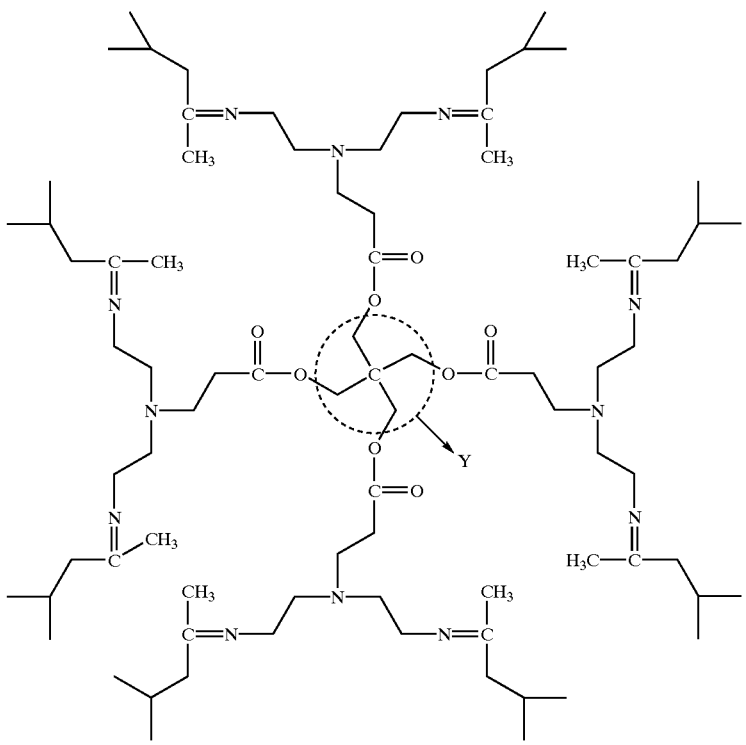

when Y is C.

The imine reactive diluent of the Formula I is produced by reacting, in the presence of a Lewis acid catalyst and a reactive solvent, an acrylate group containing organic compound having the formula:

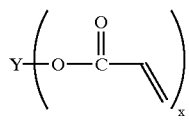

with 1.0 mole of an imine reactant per mole of acrylate groups in the compound.

The organic compound may be obtained by conventional means, such as by reacting a polyol having the desired number of functionalities with an acryloyl chloride or acrylic acid. Typically, a free radical scavenger, such as monomethyl ether hydroquinone, generally at 50 to 100 ppm of the reaction mixture, is added to prevent undesired polymerization of the resulting acrylate groups.

The imine reactant may be obtained by first dissolving a corresponding amine compound which includes $R^2$ and $R^3$ functionalities into an excess amount of a reactive solvent, generally a ketone for producing a ketimine reactive diluent and an aldehyde for producing an aldimine reactive diluent. The reactive solvent contains the desired R and $R^1$ functionalities. Some of the preferred ketones include acetone, methyl ethyl ketone, methyl pentyl ketone and preferably methyl isobutyl ketone. Some of the preferred aldehydes include propionaldehyde, butyraldehyde and isobutyraldehyde. The dissolved amine compound reacts with the reactive solvent at elevated temperatures to produce the imine reactant of the following formula:

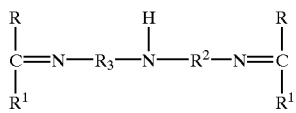

The imine reactant is then reacted with an organic compound having at least two acrylate groups to produce the imine reactive diluent. Depending upon the functionalities present on the imine reactant and the organic compound, the reaction is generally carried out at about −10° C. to 100° C., preferably, at about 0° C. to 60° C. and more preferably at about 15° C. to 35° C. in the presence of an excess amount of the reactive solvent. Typical Lewis catalyst suitably for use in the present invention is selected from at least one member of the group consisting of $FeCl_3$, acidic gamma alumina, $Yb(CF_3SO_3)_3$, $Sc(CF_3SO_3)_3$, tetraisopropyl titanate, and $La(CF_3SO_3)_3$. The amount of catalyst employable in the method of the present invention generally varies in the range of 0.01 to 20, preferably in the range of from 0.1 to 8 and more preferably in the range of from 3 to 7, all in weight percentages based on the weight of residue Y in the Formula I above. The applicants unexpectedly discovered a major improvement of the method of the present invention in that it permits one to produce the imine reactive diluent in the same reactor, without transferring the reaction mixture to any other reactors. The single reactor preparation makes the process simple-to-operate, safe and efficient.

The excess amount of the reactive solvent present in the reaction mixture is adjusted to provide a coating composition containing the imine reactive diluent of the present invention with a desired amount of VOC.

Specifically, an imine reactant may be obtained by dissolving diethylene triamine in an excess amount of 4-methyl-2-pentanone reactive solvent and then elevating the reaction mixture under reflux to about 142° C. for producing the imine reactant of the following formula:

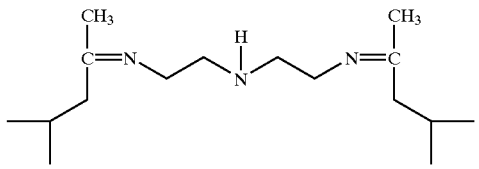

(triamine-bisketimine).

Alternatively, the foregoing triamine-bisketimine may be obtained from Air Products of Allentown, Pa. Triamine-bisketimine (imine reactant) is then reacted in the same reactor, in the presence of a Lewis catalyst with an organic compound of the following formula:

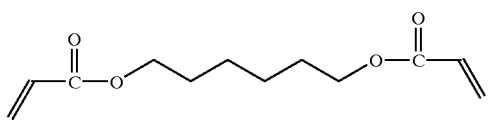

to produce the imine reactive diluent.

The present invention is also directed to a two-pack coating composition comprising a component (i) and a component (ii) wherein:

(i) comprises from 10 to 90, preferably 20 to 80 and more preferably 30 to 70 weight percent of an oligomer or a polymer having a weight average molecular weight not exceeding about 5,000, preferably 100 to 5,000, more preferably 200 to 4,500 and most preferably 300 to 4,000, and functionality selected from one or more of acetoacetate, acrylate, isocyanate, epoxide and cyclic carbonate moieties; and (ii) comprises from 10 to 90, preferably 20 to 80 and more preferably 30 to 70 weight percent of an imine reactive diluent having a weight average molecular weight from about 100 to 100,000, preferably 200 to 100,000, more preferably 250 to 50,000 and most preferably 300 to 20,000, and that is substantially free of hydrogen-bonding moieties and contains at least three imine groups per molecule wherein all percentages are based on the total weight of said components (i) and (ii).

One example of the imine reactive diluent is of the following formula:

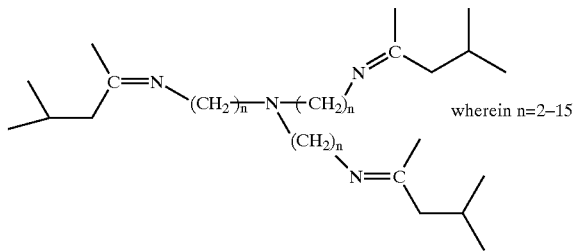

wherein n=2–15

The oligomer or polymer in the component (i) of the coating composition of the present invention are conventionally produced. A conventional acrylic polymer or oligomer, a polyester or a structured oligomer or polymer is reacted with compounds containing the desired functionalities, such as acetoacetate to produce the oligomer or polymer in the component (i). If desired the component (i) coating composition may further include a polymeric component (iii) selected from at least one of a polyacrylate, polyepoxide, polyurethane and polyester, the component having a weight average molecular weight between about 5,000 to 100,000, preferably 6,000 to 50,000 and more preferably 7,000 to 20,000, and a pendant functionality selected from at least one of acetoacetate, epoxide, isocyanate, cyclic carbonate, and acrylate moieties, the functionality comprising about 1 to 90 percent based on the weight of the monomer; the composition comprising from about 50:1 to 2, preferably 40:1 to 1:2, and more preferably 20:1 to 1:2, all by weight of said components (i+ii) to said component (iii). The polymeric component (iii) is prepared in a similar manner as to that described earlier for the oligomer or polymer used in the component (i).

The ratio of ketimine to acetoacetate, epoxide, isocyanate, cyclic carbonate, or acrylate moieties in the foregoing coating composition is in the range 5:1 to 1:5.

The foregoing coating composition preferably includes:
the component (i) comprising from 25 to 75 weight percent of the oligomer or polymer;
the component (ii) comprising from 25 to 75 weight percent of the imine reactive diluent; and
the component (iii) comprising from 1 to 50, preferably 2 to 40 weight percent of the polyester polyol or polyacrylic polyol.

In the foregoing coating composition the oligomer or polymer of the component (i) is functionalized with acetoacetate moieties;
the imine reactive diluent of the component (ii) is functionalized with ketimine moieties; and
the polyester polyol or polyacrylic polyol of the component (iii) is functionalized with acetoacetate moieties.

The present invention is also directed to a two-pack coating composition comprising a component (i) and a component (ii) wherein:

(i) comprises from 10 to 90 weight percent of an oligomer or a polymer having a molecular weight not exceeding about 5,000 and functionality selected from one or more of acetoacetate, acrylate, isocyanate, epoxide and cyclic carbonate moieties; and (ii) comprises from 10 to 90 weight percent of an imine reactive diluent of Formula I described earlier.

If desired, The component (i) of the foregoing coating composition may further include the polymeric component (iii) described earlier.

The present invention is also directed to a method of producing a coating on a substrate comprising:
admixing the components (i) and (ii) of the coating composition described above to form a pot mix;
applying a layer of the pot mix on the substrate;
curing the layer to form the coating.

The inventors unexpectedly found that by including the highly reactive imine reactive diluents having low viscosity in a low VOC, high solids coating composition of the present invention, especially in an automotive refinish application, a layer from a pot mix of the containing composition can be readily applied by conventional means. Moreover, the layer dries at a very rapid rate, which is very important in an automotive, refinish environment.

Aldimine and ketimine reactive diluents having multi-imine functionality are disclosed. These highly reactive compositions are further characterized as having substantially no hydrogen bonding sites that can cause an undesirable increase in solution viscosities when employed as components of coating compositions. The imine reactive diluents of this invention (ketimines and aldimines) are characterized by the absence of hydrogen atoms on the nitrogen or oxygen atoms, which contributes to maintenance of good coating viscosities.

DETAILS OF THE INVENTION

As used Herein:

"Two-pack coating composition" means a thermosetting composition comprising two components that are stored in separate containers, which are typically sealed for increasing the shelf life of the components of the coating composition. The components are mixed just prior to use to form a pot mix, which has a limited pot life, typically a few minutes, such as 15 minutes to 45 minutes to a few hours, such as 2 hours to 6 hours. The pot mix is applied as a layer of desired thickness on a substrate surface, such as an autobody. After application, the layer dries and cures to form a coating on the substrate surface having desired coating properties, such as solvent resistance. "Low VOC coating composition" means a coating composition that is less than about 0.6 kilogram of organic solvent per liter (5 pounds per gallon) of the composition, as determined under the procedure provided in ASTM D3960. The amount of organic solvent used in the present invention results in the composition having a VOC of less than 0.6 kilogram (5 pounds per gallon) and preferably in the range of 0.012 kilogram to 0.528 kilogram (0.1 pounds to 4.4 pounds per gallon), more preferably in the range of from 0.12 kilogram to 0.42 kilogram (1.0 to 3.5 pounds per gallon) of organic solvent per liter of the composition.

"High solids composition" means a coating composition having a solids component of above 30 percent, preferably in the range of from 40 to 95 percent and more preferably in the range of from 45 to 80 percent, all in weight percentages based on the total weight of the composition.

"GPC weight average molecular weight" means a weight average molecular weight measured by utilizing gel permeation chromatography. A high performance liquid chromatograph (HPLC) supplied by Hewlett-Packard, Palo Alto, Calif. was used. Unless stated otherwise, the liquid phase used was tetrahydrofurane and the standard was polymethyl methacrylate.

"Polymer Solids", "Binder solids" or "Oligomer solids" means a polymer or binder or oligomer in its dry state.

"Structured oligomer or polymer" means a structured molecule, such as a macromolecule, oligomer or polymer, which unlike conventional resins, has a very well defined structure, such as star, expanded star, dendritic (hyper branched), or cyclodextrinic structured molecules.

"Hydrogen bonding group" means a group containing a heteroatom that is bonded to a hydrogen atom. For example, O, S or N.

"Residue" means a fragment that is a compound, oligomer or a polymer.

Imine Reactive Diluents

Representative imine reactive diluents of this invention are typically advantageously prepared in a single reactor by the following procedure. A three neck flask equipped with a magnetic stirrer, Dean-Stark trap and condenser, thermometer, oil heating bath and an Argon (Ar) inlet and outlet is charged with a triamine (0.50 mol) having two primary amine termini and an internal, aliphatic secondary amine group, and an aldehyde or ketone (1.22 mol) suitable for use in an imine-forming reaction. The solution is heated to reflux under Ar and water is removed azeotropically via the Dean-Stark trap. The mixture is cooled to room temperature and a reagent containing two, three or more acrylate groups is then added to the reaction flask wherein bisketimine to acrylate is about 1:1 by moles. The resulting mixture is stirred under Ar in the presence of a Lewis acid catalyst until residual acrylate in the reaction mixture is no longer detectable by $^1$H NMR spectroscopy. The product is then filtered under Ar to remove the catalyst.

Coatings

As referred earlier, the preferred coating compositions comprise from 25 to 75 weight percent of component (i), from 25 to 75 weight percent of component (ii), and 0 weight percent of component (iii), based on a total of 100 weight percent. Other preferred compositions have similar amounts of components (i) and (ii) but component (iii) will be present at 1 to 50, more preferably 2 to 40 weight percent. Specific preferred oligomers (i) are structured and unstructured polyesters and polyacrylics that contain pendant acetoacetate or acrylate moieties; preferred oligomers (ii) are of Formula 1 (wherein x=2, 3 or 4); and preferred polymeric components (iii) are polyesters and polyacrylics that contain acetoacetate or acrylate pendant moieties.

Representative coatings containing imines of this invention are generally prepared by combining the imines with complementary coating-formation ingredients that will be obvious to one having ordinary skill in this art.

The imine reactive diluents of this invention provide the following advantages over conventional materials:

(i) they are formed from unhindered amines, therefore reactive amine end groups are generated after unblocking (loss of ketone or aldehyde). This results in rapid reaction with electrophiles;

(ii) they are multifunctional (3 or more). This makes them orders of magnitude higher in reactivity than difunctional compounds; and (iii) they do not contain H-bonding moieties and, as a result, provide dramatically lower solution viscosities at high solids (e.g., $\geq$65 percent wt. solids) and can be applied via conventional spray guns. This attribute is particularly important for low VOC coatings.

These imine reactive diluents contain all three of the attributes described above, while conventional imines are either difunctional and do not contain H-bonding moieties, which results in very slow reaction with electrophiles, or they are multifunctional but contain H-bonding moieties which precludes their use in high solids, low VOC coatings due to their high solution viscosities. The compositions of this invention are characterized by being quick-drying, having low solution viscosity, and cured films made from them have good solvent resistance.

The coating composition of the present invention may also contain conventional additives, such as pigments, stabilizers, rheology control agents, flow agents, toughening agents and fillers. Such additional additives will, of course, depend on the intended use of the coating composition. Fillers, pigments, and other additives that would adversely effect the clarity of the cured coating will not be included if the composition is intended to be used as a clear coating. The foregoing additives may be added to either the component (i) or the component (ii), or both, depending upon the intended use of the coating composition.

EXAMPLES, COMPARISONS AND PREPARATIONS

Persoz hardness values for the following Examples and Comparisons are presented in Table 1.

Preparation 1

Diacetoacetate A

The following was added to a glass reactor equipped with a thermometer, stirrer, nitrogen blanket, vigreux column, condenser, distillation adapter and receiver:

| Ingredient | Parts By Weight |
| --- | --- |
| ethoxylated Bisphenol A (SynFac 8024; Sartomer Chemical) | 100 |
| tert-butylacetoacetate | 88 |

The mixture was heated to reflux and 41.2 parts of tert-butyl alcohol were removed by distillation (the maximum batch temperature was 180° C.). The batch was cooled and had the following properties:

Solids=98.81%; Gardner-Holdt viscosity=Z2+½.

Preparation 2

Tetracetoacetate B

The following was added to a glass reactor equipped with a thermometer, stirrer, nitrogen blanket, vigreux column, condenser, distillation adapter and receiver:

| Ingredient | Parts By Weight |
| --- | --- |
| pentaerythritol | 100 |
| tert-butylacetoacetate | 464.7 |

These ingredients were heated to boiling and 217.6 parts of tert-butyl alcohol were removed by atmospheric distillation (the maximum batch temperature was 180° C.). The batch was cooled and had the following properties:

The solids was 97.18%; the Gardner-Holdt viscosity=Q+½.

Preparation 3

Synthesis of Polyester (AcAc) C

The following materials were charged to a 5 liter reactor equipped with 10" packed separation column, water separator and condenser while being purged with nitrogen; 946.1 parts neopentyl glycol, 270.4 parts trimethylol propane, 787.1 parts isophthalic acid, 701.75 parts of o-phthalic anhydride, 0.7 parts hydrated monobutyl tin oxide, 100 parts water and 83.68 parts toluene. The mixture was heated slowly over 9.5 hours to 230° C. while distilling 356 g water (theoretical 356.06 g). The temperature was reduced to 75° C. and 966.32 parts xylene and 817.24 g TBAA were added. The temperature was then increased to 140° C. and stirred for 3 hours while removing 404 g liquid (theoretical 382.76). The mixture was then cooled to room temperature.

Preparation 4

Synthesis of Polyacrylic (AcAc) D

To a reactor 273.34 parts butyl acetate were charged and heated to boiling (ca. 125° C.) under nitrogen atmosphere. Subsequently a mixture of 160.92 parts styrene, 201.1 parts acetoacetoxyethyl methacrylate, 40.2 parts hydroxyethyl acrylate, and 27 parts butyl acetate were added over a period of 210 minutes. At the same time, 21.5 parts t-butylperoxy acetate in mineral spirits (75% solids), and 71.87 parts butyl acetate were added over a period of 270 minutes. The reaction mixture was held an additional 60 minutes at boiling after the feeds were complete. After the hold period, an additional 30 parts butyl acetate was added and the mixture cooled to room temperature.

Functionalized Oligomers (i) and Polymers (iii)

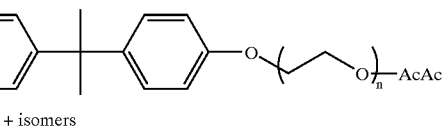

A

+ isomers

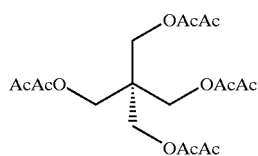

B

Polyester (AcAc) (contains pendant AcAc groups) C (iii)
Polyacrylic (AcAc) (contains pendant AcAc groups) D (iii)
Pentaerythritol tetraacrylate E (i)
Epoxide=Epon 1001 (diepoxide oligomer from bisphenol A and epichlorohydrin) F (i)
Isocyanate=Tolonate HDT (oligomer from hexamethylene diisocyanate) G (i)

Ketimine Oligomers (ii)

The following oligomers and polymers are employed in the Comparisons and Examples which follow:

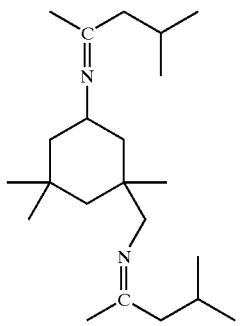
A (not of the invention)
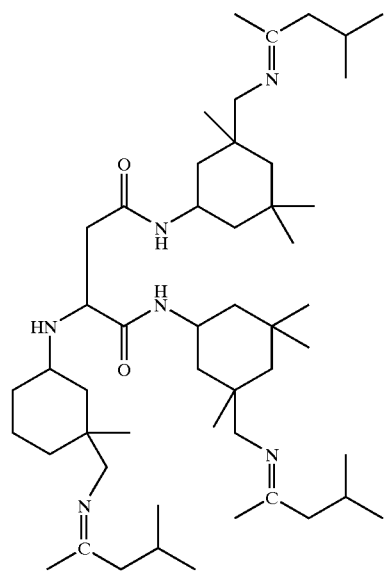
+ isomers
B (not of the invention)
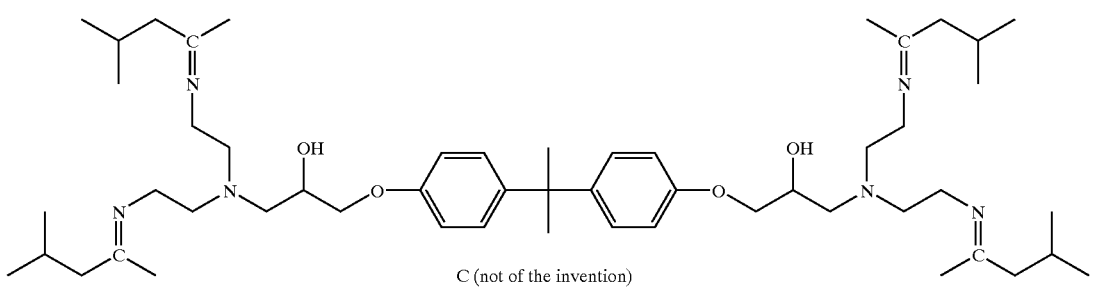
C (not of the invention)
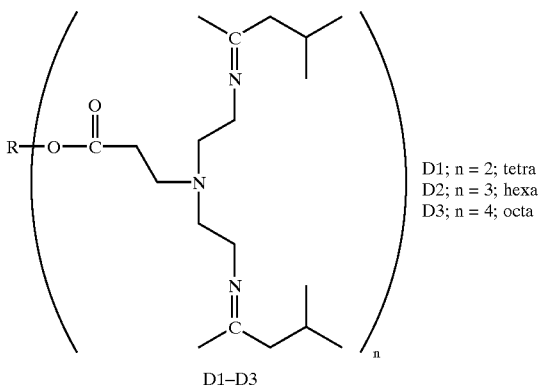
D1; n = 2; tetra
D2; n = 3; hexa
D3; n = 4; octa
D1–D3
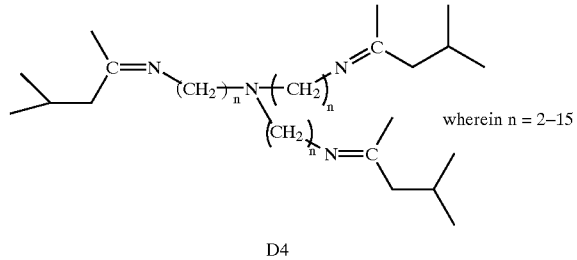
wherein n = 2–15
D4
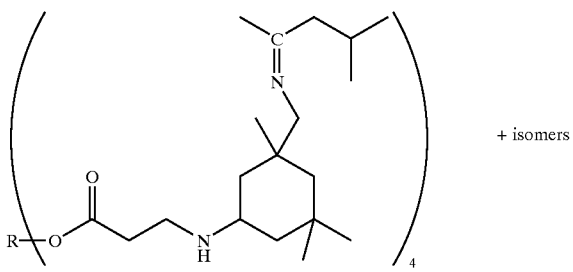
+ isomers
E (not of the invention)

Comparison 1a

A coating composition was prepared by successively mixing 15.6 parts of diacetoacetate A, 12.7 parts diketimine from isophorone diamine and methylisobutyl ketone (MIBK) (bisketimine A), 24.5 parts butyl acetate, 15 parts xylenes and 2.3 parts methylisobutyl ketone. The resulting mixture was applied to a cold-rolled steel panel via a doctor blade to give a coating thickness of approximately 40 $\mu$m after drying.

Comparison 1b

A coating composition was prepared by successively mixing 15.6 parts of diacetoacetate A, 27 parts trisketimine prepared from 1 mol dimethylmaleate, 3 moles of isophorone diamine and 3 moles MIBK (trisketimine B; applied as a 78% solids in MIBK), 28.2 parts butyl acetate, 18 parts xylenes and 2.3 parts MIBK. The resulting mixture was applied to a cold-rolled steel panel via a doctor blade to give a coating thickness of approximately 40 $\mu$m after drying.

Comparison 1c

A coating composition was prepared by successively mixing 15.6 parts of diacetoacetate A, 32.8 parts tetraketimine prepared from 1 mol of the diglycidyl ether of Bisphenol A and 2 moles of the bisketimine of diethylene triamine (tetraketimine C; applied as a 55% solids solution), 19.9 parts butyl acetate, 13 parts xylenes and 2.3 parts MIBK. The resulting mixture was applied to a cold-rolled steel panel via a doctor blade to give a coating thickness of approximately 40 $\mu$m after drying.

Example 1

A coating composition was prepared by successively mixing 15.6 parts of diacetoacetate A, 30 parts tetraketimine prepared from 1 mol of a 1,6 hexanediol diacrylate and 2 moles of the bisketimine of diethylene triamine (tetraketimine D1; 70% solids in MIBK), 22 parts butyl acetate, 14 parts xylenes and 2.3 parts methylisobutyl ketone. The resulting mixture was applied to a cold-rolled steel panel via a doctor blade to give a coating thickness of approximately 40 $\mu$m after drying.

Comparison 2a

A coating composition was prepared by successively mixing 10.3 parts of tetraacetoacetate B, 18 parts diketimine from isophorone diamine and methylisobutyl ketone (MIBK) (bisketimine A), 24.2 parts butyl acetate, 15.3 parts xylenes and 2.3 parts methylisobutyl ketone. The resulting mixture was applied to a cold-rolled steel panel via a doctor blade to give a coating thickness of approximately 40 $\mu$m after drying.

Comparison 2b

A coating composition was prepared by successively mixing 10.3 parts of tetraacetoacetate B, 39.5 parts trisketimine prepared from 1 mol dimethylmaleate, 3 moles of isophorone diamine and 3 moles MIBK (trisketimine B; applied as a 78% solids in MIBK), 30 parts butyl acetate, 20 parts xylenes and 2.3 parts MIBK. The resulting mixture was applied to a cold-rolled steel panel via a doctor blade to give a coating thickness of approximately 40 $\mu$m after drying.

Comparison 2c

A coating composition was prepared by successively mixing 10.3 parts of tetraacetoacetate B, 47.9 parts tetraketimine prepared from 1 mol of the diglycidyl ether of Bisphenol A and 2 moles of the bisketimine of diethylene triamine (tetraketimine C; applied as a 55% solids solution), 18 parts butyl acetate, 12 parts xylenes and 2.3 parts MIBK. The resulting mixture was applied to a cold-rolled steel panel via a doctor blade to give a coating thickness of approximately 40 $\mu$m after drying.

Comparison 2d

A coating composition was prepared by successively mixing 10.3 parts of tetraacetoacetate B, 48.5 parts tetraketimine prepared from 1 mol pentaerythritol tetraacrylate, 4 moles isophorone diamine and 4 moles MIBK (tetraketimine E), 18 parts butyl acetate, 12 parts xylenes and 2.3 parts methylisobutyl ketone. The resulting mixture was applied to a cold-rolled steel panel via a doctor blade to give a coating thickness of approximately 40 $\mu$m after drying.

Example 2

A coating composition was prepared by successively mixing 10.3 parts of tetraacetoacetate B, 30 parts tetraketimine prepared from 1 mol of a 1,6 hexanediol diacrylate and 2 moles of the bisketimine of diethylene triamine (tetraketimine D1, 70% solids in MIBK), 21 parts butyl acetate, 14 parts xylenes and 2.3 parts methylisobutyl ketone. The resulting mixture was applied to a cold-rolled steel panel via a doctor blade to give a coating thickness of approximately 40 $\mu$m after drying.

Example 3

A coating composition was prepared by successively mixing 10.3 parts of tetraacetoacetate B, 28.9 parts tetraketimine prepared from 1 mol of a trimethanol propane triacrylate and 3 moles of the bisketmine of diethylenetriamine (hexaketimine D2; 70% solids in MIBK), 20.4 parts butylacetate, 14 parts xylenes and 2.3 parts methylisobutyl ketone. The resulting mixture was applied to a cold-rolled steel panel via a doctor blade to give a coating thickness of approximately 40 $\mu$m after drying.

Example 4

A coating composition was prepared by successively mixing 10.3 parts of tetraacetoacetate B, 28.0 parts octaketimine prepared from 1 mol of pentaerythritol tetraacrylate and 4 moles of the bisketmine of diethylenetriamine (octaketimine D3; 70% solids in MIBK), 20.4 parts butylacetate, 13 parts xylenes and 2.3 parts methylisobutyl ketone. The resulting mixture was applied to a cold-rolled steel panel via a doctor blade to give a coating thickness of approximately 40 $\mu$m after drying.

Example 5

A coating composition was prepared by successively mixing 4.8 parts of tetraacetoacetate B, 6.3 parts polyester (AcAc) C, 18.7 parts tetraketimine prepared from 1 mol of 1,6-hexanediol diacrylate and 2 moles of the bisketmine of diethylene triamine (tetraketimine D1; 70% solids in MIBK) and 15.2 parts butyl acetate. The resulting mixture was applied to a cold-rolled steel panel via a doctor blade to give a coating thickness of approximately 40 $\mu$m after drying.

Example 6

A coating composition was prepared by successively mixing 4.8 parts of tetraacetoacetate B, 11.8 parts polyacrylate (AcAc) D, 18.7parts tetraketimine prepared from 1 mol of 1,6-hexanediol diacrylate and 2 moles of the bisketmine of diethylene triamine (tetraketimine D1; 70% solids in MIBK) and 11.9 parts butyl acetate. The resulting mixture was applied to a cold-rolled steel panel via a doctor blade to give a coating thickness of approximately 40 μm after drying.

Example 7

A coating composition was prepared by successively mixing 2.1 parts of tetraacetoacetate B, 8.1 parts Epon 1001 (Shell), 6.3 parts tetraketimine prepared from 1 mol of 1,6-hexanediol diacrylate and 2 moles of the bisketmine of diethylene triamine (tetraketimine D1; 70% solids in MIBK) and 8.53 parts butyl acetate. The resulting mixture was applied to a cold-rolled steel panel via a doctor blade to give a coating thickness of approximately 40 μm after drying.

Example 8

A coating composition was prepared by successively mixing 3.25 parts of pentaerythritol tetraacrylate E (Sarotmer SR295), 6.3 parts polyester(AcAc) C,18.7 parts tetraketimine prepared from 1 mol of 1,6-hexanediol diacrylate and 2 moles of the bisketmine of diethylene triamine (tetraketimine D1; 70% solids in MIBK) and 14.2 parts butyl acetate. The resulting mixture was applied to a cold-rolled steel panel via a doctor blade to give a coating thickness of approximately 40 μm after drying.

Example 9

A coating composition was prepared by successively mixing 3.25 parts of pentaerythritol tetraacrylate E (Sartomer SR295), 11.8 parts polyacrylate (AcAc)D, 18.7 parts tetraketimine prepared from 1 mol of 1,6-hexanedioldiacrylate and 2 moles of the bisketmine of diethylene triamine (tetraketimine D1; 70% solids in MIBK) and 10.9 parts butyl acetate. The resulting mixture was applied to a cold-rolled steel panel via a doctor blade to give a coating thickness of approximately 40 μm after drying.

Example 10

A coating composition was prepared by successively mixing 5.86 parts of tetraacetoacetate B, 1.42 parts Isocyanate G (Tolonate HDT;Rhone-Poulenc), 10.1 parts tetraketimine prepared from 1 mol of 1,6-hexanediol diacrylate and 2 moles of the bisketmine of diethylene triamine (tetraketimine D1; 70% solids in MIBK) and 11 parts butyl acetate. The resulting mixture was applied to a cold-rolled steel panel via a doctor blade to give a coating thickness of approximately 40 μm after drying.

Example 11

A coating composition was prepared by successively mixing 3.3 parts of tetraacetoacetate B, 16.8 parts isocyanate G (Tolonate HDT; Rhone-Poulenc), 13.2 parts bisketimine prepared from isophorone diamine and 2 moles of MIBK (bisketimine A; 100% solids), 2.4 parts tetraketimine prepared from 1 mol of 1,6-hexanediol diacrylate and 2 moles of the bisketmine of diethylene triamine (tetraketimine D1; 70% solids in MIBK) and 11 parts butyl acetate. The resulting mixture was applied to a cold-rolled steel panel via a doctor blade to give a coating thickness of approximately 40 μm after drying.

Example 12

A coating composition was prepared by successively mixing 12.4 parts of tetraacetoacetate B, 20 parts triketimine prepared from 1 mol of tris(aminoethyl) amine and 3.9 moles of MIBK (Triketimine D4; n=2; 90.4% solids in MIBK) and 21.7 parts butyl acetate. The resulting mixture was applied to a cold-rolled steel panel via a doctor blade to give a coating thickness of approximately 58 μm after drying.

Example 13

A coating composition was prepared by successively mixing 10.2 parts of tetraacetoacetate B, 42 parts polyacrylate(AcAc) D, 20 parts triketimine prepared from 1 mol of tris(aminoethyl) amine and 3.9 moles of MIBK (Triketimine D4; n=2; 90.4% solids in MIBK) and 12.6 parts butyl acetate. The resulting mixture was applied to a cold-rolled steel panel via a doctor blade to give a coating thickness of approximately 58 μm after drying.

Tables 1–3 summarize the reaction of a number of ketimine functionalized compounds (ii; A–C, D1–D4 and E) with various oligomers and/or polymers (i and iii; A–G) that contain the appropriate complementary functional group(s) (e.g., acetoacetate, acrylate, epoxide and isocyanate). The reaction rates to form cross-linked films are monitored by measuring film hardness versus time using a Persoz instrument. Persoz hardness values obtained for films that have cured for 3 hours are shown.

Table 1 illustrates the importance of the degree of ketimine functionality in determining cure rate, where higher functionality leads to more rapid cure. For example, if the acetoacetate building block is held constant by using difunctional acetoacetate A, than the cure rate increases with increasing ketimine functionality as shown [(Example 1) and (Comparison 1c)>(Comparison 1b) and (Comparsion 1a)]. In addition, the importance of hydrogen bonding moieties is also shown, since only ketimine D1 of our invention shows acceptable cure rate and does not have hydrogen bonding moieties. Hydrogen bonding moieties dramatically increase solution viscosity in high solids coatings formulations (> about 60 to 70% solids).

TABLE 1

| Example or Comparison | Ketimine and Functionality | Acetoacetate and Functionality | H-Bonding Moieties in Ketimine | Persoz Hardness (T = 3 h) |
|---|---|---|---|---|
| Comparison 1a | A (Difunctional) | A (Difunctional) | No | Tacky |
| Comparison 1b | B (Trifunctional) | A (Difunctional) | Yes* | Tacky |
| Comparison 1c | C (Tetrafunctional) | A (Difunctional) | Yes* | 38 |
| Example 1 | D1 (Tetrafunctional) | A (Difunctional) | No | 29 |

*Viscosity is too high to use in high solids coatings compositions (>60 to 70% solids)

Table 2 shows additional examples of this phenomenon. In this case, a tetrafunctional acetoacetate diluent B is used instead of difunctional acetoacetate diluent A. It is clear that Comparison 2a yields a film that cures very slowly because the resulting film is still "tacky" after 3 hours cure. For lower molecular weight building blocks such as those of the present invention, cure via the formation of covalent bonds is needed to prepare robust films. This behavior is attributable to the ketimine being only difunctional. Comparisons 2b, 2c, 2d provide films that cure significantly faster because the ketimines are tri or tetrafunctional, however, the presence of hydrogen bonding moieties leads to very high solution viscosities as shown by the #2 Zahn readings at T=0, 30 and 60 minutes. Again, only examples of the invention herein provide rapid cure and low solution viscosities as is shown in examples 2–4. The difference in solution viscosity of examples 2, 3 and 4 versus Comparisons 2b, 2c, 2 d is attributable to the lack of hydrogen bonding moieties.

TABLE 2

| Example or Comparison | Ketimine and Functionality | Acetoacetate and Functionality | H-Bonding Moieties in Ketimine | Persoz Hardness (T - 3h) | #2 Zahn Readings at 77% solids (s-seconds) |
|---|---|---|---|---|---|
| Comparison 2a | A (Difunctional) | B (Tetrafunctional) | No | Tacky | T = 0; 18 s<br>T = 30 min; 18 s<br>T = 60 min; 18 s |
| Comparison 2b | B (Trifunctional) | B (Tetrafunctional) | Yes* | 22 | T = 0; >60 s<br>T = 20 min; >60 s<br>T = 60 min; >60 s |
| Comparison 2c | C (Tetrafunctional) | B (Tetrafunctional) | Yes* | 76 | T = 0; >60 s<br>T = 30 min; >60 s<br>T = 60 min; >60 s |
| Comparison 2d | E (Tetrafunctional) | B (Tetrafunctional) | Yes* | 10 | T = 0; >60 s<br>T = 30 min; >60 s<br>T = 60 min; >60 s |
| Example 2 | D1 (Tetrafunctional) | B (Tetrafunctional) | No | 50 | T = 0; 25 s<br>T = 30 min; 28 s<br>T = 60 min; 28 s |
| Example 3 | D2 (Hexafunctional) | B (Tetrafunctional) | No | 68 | |
| Example 4 | D3 (Octafunctional) | B (Tetrafunctional) | No | 133 | |

*Viscosity is too high

Table 3 illustrates the wide variety of acetoacetate, acrylate, epoxide and isocyanate-functionalized building blocks that can also be reacted with the new ketimine(s) to form robust thermoset coatings.

TABLE 3

| Example | Ketimine and Functionality | Acetoacetate and Functionality | H-Bonding Moieties in Ketimine | Persoz Hardness (T = 3 h) |
|---|---|---|---|---|
| 5 | D1 (Tetrafunctional) | B (Tetrafunctional)<br>+<br>Polyester (AcAc) C | No | 28 |
| 6 | D1 (Tetrafunctional) | B (Tetrafunctional)<br>+<br>Polyacrylate (AcAc) D | No | 43 |
| 7 | D1 (Tetrafunctional) | B (Tetrafunctional)<br>+<br>Epoxide F (Epon 1001) | No | 21 |
| 8 | D1 (Tetrafunctional) | Tetraacrylate E (Tetrafunctional)<br>+<br>Polyester (AcAc) C | No | 32 |
| 9 | D1 (Tetrafunctional) | Tetraacrylate E (Tetrafunctional)<br>+<br>Polyacrylate (AcAc) D | No | 26 |
| 10 | D1 (Tetrafunctional) | B (Tetrafunctional)<br>+<br>Isocyanate G (Tolonate HDT) | No | 42 |
| 11 | D1 (Tetrafunctional)<br>+<br>A (Difunctional) | B (Tetrafunctional)<br>+<br>Isocyanate G (Tolonate HDT) | No | 35 |
| 12 | D4 (Trifunctional) | B (Tetrafunctional) | No | 80 |
| 13 | D4 (Trifunctional) | B (Tetrafunctional)<br>+<br>Polyacrylate (AcAc) D | No | 50 |

Example 14
Tetraketimine (Single Reactor Prep; FeCl₃ Catalyst)

A three neck flask equipped with a magnetic stirrer, Dean-Stark trap and condenser, thermometer, oil heating bath and an Ar inlet and outlet was charged with diethylene triamine (47.25 g, 0.458 mol) and 4-methyl-2-pentanone (122.25 g, 1.22 mol). The mixture was heated to reflux under Ar and water was removed azeotropically via the Dean-Stark trap. The reflux was continued until the reaction temperature reached 142° C. The mixture was cooled to room temperature and 1,6-hexanediol diacrylate (52.3 g, 0.229 mol) and the iron (III) chloride catalyst (1.25 g) were then added to the reaction flask. The resulting mixture was stirred under Ar at room temperature for 48 h and then filtered under Ar to remove the catalyst.

Example 15
Tetraketimine (Single Reactor Prep; Sc(CF₃SO₃)₃ Catalyst)

A three neck flask equipped with a magnetic stirrer, Dean-Stark trap and condenser, thermometer, oil heating bath and an Ar inlet and outlet was charged with diethylene triamine (47.25 g, 0.458 mol) and 4-methyl-2-pentanone (122.25 g, 1.22 mol). The mixture was heated to reflux under Ar and water was removed azeotropically via the Dean-Stark trap. the reflux was continued until the reaction temperature reached 142° C. The mixture was cooled to room temperature and 1,6-hexanediol diacrylate (52.3 g, 0.229 mol) and Sc(CF₃SO₃)₃ catalyst (2.62 g) were then added to the reaction flask. The resulting mixture was stirred under Ar at room temperature for 48 h and then filtered under Ar to remove the catalyst.

Example 16
Tetraketimine (Single Reactor Prep; 10 wt. % FeCl₃ on Alumina Catalyst)

A three neck flask equipped with a magnetic stirrer, Dean-Stark trap and condenser, thermometer, oil heating bath and an Ar inlet and outlet was charged with diethylene triamine (47.25 g, 0.458 mol) and 4-methyl-2-pentanone (122.25 g, 1.22 mol). The mixture was heated to reflux under Ar and water was removed azeotropically via the Dean-Stark trap. The reflux was continued until the reaction temperature reached 142° C. The mixture was cooled to room temperature and 1,6-hexanediol diacrylate (52.3 g, 0.229 mol) and the iron (III) chloride catalyst (16 g, 10 wt. % on alumina) were then added to the reaction flask. The resulting mixture was stirred under Ar at room temperature for 48 h and then filtered under Ar to remove the catalyst.

Example 17
Tetraketimine (Single Reactor Prep; 5 wt. % FeCl₃ on Silica Catalyst)

A three neck flask equipped with a magnetic stirrer, Dean-Stark trap and condenser, thermometer, oil heating bath and an Ar inlet and outlet was charged with diethylene triamine (47.25 g, 0.458 mol) and 4-methyl-2-pentanone (122.25 g, 1.22 mol). The mixture was heated to reflux under Ar and water was removed azeotropically via the Dean-Stark trap. The reflux was continued until the reaction temperature reached 142° C. The mixture was cooled to room temperature and 1,6-hexanediol diacrylate (52.3 g, 0.229 mol) and the iron (III) chloride catalyst (25 g, 5 wt. % on silica) were then added to the reaction flask. The resulting mixture was stirred under Ar at room temperature for 48 h and then filtered under Ar to remove the catalyst.

Example 18
Hexaketimine (Single Reactor Prep; 5 wt. % FeCl₃ on Silica Catalyst)

A three neck flask equipped with a magnetic stirrer, Dean-Stark trap and condenser, thermometer, oil heating bath and an Ar inlet and outlet was charged with diethylene triamine (47.25 g, 0.458 mol) and 4-methyl-2-pentanone (122.25 g, 1.22 mol). The mixture was heated to reflux under Ar and water was removed azeotropically via the Dean-Stark trap. The reflux was continued until the reaction temperature reached 142° C. The mixture was cooled to room temperature and trimethanol propane triacrylate (45.24 g, 0.153 mol) and the iron(III) chloride catalyst (25 g, 5 wt. % on silica) were added to the reaction flask. The resulting mixture was stirred under Ar at room temperature for 48 h and then filtered under Ar to remove the catalyst.

Example 19
Octaketimine (Single Reactor Prep; 5 Weight Percent FeCl₃ on Silica Catalyst)

A three neck flask equipped with a magnetic stirrer, Dean-Stark trap and condenser, thermometer, oil heating bath and an Ar inlet and outlet was charged with diethylene triamine (47.25 g, 0.458 mol) and 4-methyl-2-pentanone (122.25 g, 1.22 mol). The mixture was heated to reflux under Ar and water was removed azeotropically via the Dean-Stark trap. The reflux was continued until the reaction temperature reached 142° C. The mixture was cooled to room temperature and pentaerythritol tetraacrylate (40.34 g, 0.114 mol) and the iron(III) chloride catalyst (25 g, 5 wt. % on silica) were then added to the reaction flask. The resulting mixture was stirred under Ar at room temperature for 48 h and then filtered under Ar to remove the catalyst.

What is claimed is:

1. A two-pack coating composition comprising a component (i) and a component (ii) wherein:

(i) comprises from 10 to 90 weight percent of an oligomer or a polymer having a molecular weight not exceeding about 5,000 and functionality selected from one or more of acetoacetate, acrylate, isocyanate, epoxide and cyclic carbonate moieties; and (ii) comprises from 10 to 90 weight percent of an imine reactive diluent having the following formula:

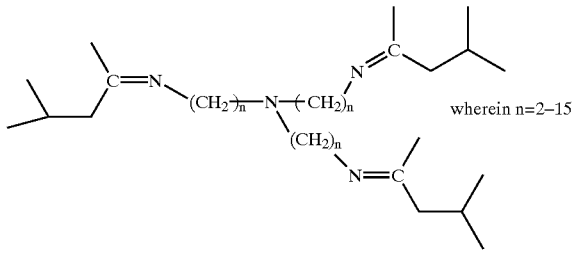

wherein n=2–15 wherein all percentages are based on the total weight of said components (i) and (ii).

2. The coating composition of claim 1 wherein said component (i) further comprises a polymeric component (iii) selected from at least one of a polyacrylate, polyepoxide, polyurethane and polyester, the component having a weight average molecular weight between about 5,000 to 100,000 and a pendant functionality selected from the group consisting of at least one of acetoacetate, acrylate, epoxide, isocyanate, or cyclic carbonate moieties, the functionality comprising about 10 to 90 percent based on the weight of the monomer; the composition comprising from about 50:1 to 1:2 by weight of said components (i+ii) to said component (iii).

3. The coating composition of claim 1 where the ratio of ketimine to said acetoacetate, acrylate, epoxide, isocyanate, or cyclic carbonate moieties is in the range 5:1 to 1:5.

4. The coating composition of claim 2 wherein:
   said component (i) comprises from 25 to 75 weight percent of said oligomer or polymer;
   said component (ii) comprises from 25 to 75 weight percent of said imine reactive diluent; and
   said component (iii) comprises from 1 to 50 weight percent of said polyester polyol or polyacrylic polyol.

5. The coating composition of claim 4 wherein:
   said oligomer or polymer of said component (i) is functionalized with acetoacetate moieties; and
   said polyester polyol or polyacrylic polyol of said component (iii) is functionalized with acetoacetate moieties.

6. A method for making the coating composition of claim 1 comprising admixing the components (i), and (ii).

7. A method of producing a coating on a substrate comprising:
   admixing the components (i) and (ii) of the coating composition of claim 1 or 2 to form a pot mix;
   applying a layer of said pot mix on said substrate;
   curing said layer to form said coating.

8. A method of producing a coating on a substrate comprising:
   admixing the components (i) and (ii) of the coating composition of claim 1 or 2 to form a pot mix;
   applying a layer of said pot mix on said substrate;
   curing said layer to form said coating.

* * * * *